United States Patent
Gooden

(10) Patent No.: US 7,169,129 B2
(45) Date of Patent: Jan. 30, 2007

(54) APPARATUS AND METHOD FOR PERFORMING A TRACHEOTOMY

(76) Inventor: Rodney S. Gooden, 439 Cape Rd., Carnesville, GA (US) 30521

(*) Notice: Subject to any disclaimer, the term of this patent is extended or adjusted under 35 U.S.C. 154(b) by 76 days.

(21) Appl. No.: 10/970,021

(22) Filed: Oct. 21, 2004

(65) Prior Publication Data

US 2005/0039755 A1 Feb. 24, 2005

(51) Int. Cl.
*A61M 5/178* (2006.01)
*A61M 25/00* (2006.01)
*A61M 16/00* (2006.01)

(52) U.S. Cl. ............. 604/164.02; 604/265; 128/207.29

(58) Field of Classification Search ........... 128/207.14, 128/207.15, 200.26; 600/101, 185; 606/45, 606/108, 167, 184; 604/93.01, 112, 96.01, 604/104, 103.01, 103.07, 118, 167.01, 164–167
See application file for complete search history.

(56) References Cited

U.S. PATENT DOCUMENTS

| | | | |
|---|---|---|---|
| 3,643,649 A | 2/1972 | Amato | |
| 3,886,946 A | 6/1975 | Hyde | |
| 4,291,690 A | 9/1981 | Jessen | |
| 4,877,021 A | 10/1989 | Higer | |
| 5,669,885 A * | 9/1997 | Smith | .......... 606/184 |
| 5,967,143 A | 10/1999 | Klappenberger | |
| 6,298,851 B1 | 10/2001 | Parota | |
| 2004/0035432 A1 | 2/2004 | Gostelow | |

* cited by examiner

*Primary Examiner*—Henry Bennett
*Assistant Examiner*—Shumaya B. Ali
(74) *Attorney, Agent, or Firm*—Withers & Keys, LLC

(57) ABSTRACT

Apparatus and methods provide for a tracheotomy to be performed on a patient. The apparatus includes an applicator base with an aperture placed over the trachea. A firing mechanism is triggered by application of manual force to an actuator to propel a cutting instrument and grommet through the aperture of the applicator base to insert the grommet into the trachea. A supply of breathable gas may be provided through an air passage of the grommet and into the trachea and lungs of the patient. The methods provide for placing an applicator base of a tracheotomy device onto the neck of the patient so that a curvature of the applicator base fits to the curvature of the trachea and so that an aperture is over the trachea.

20 Claims, 9 Drawing Sheets

APPARATUS AND METHOD FOR PERFORMING A TRACHEOTOMY

TECHNICAL FIELD

The present invention is related to performing a tracheotomy on a patient. More specifically, the present invention is related to apparatus and methods for performing a tracheotomy involving triggering a firing mechanism to propel a cutting instrument and grommet toward the trachea and to insert the grommet within the trachea of the patient.

BACKGROUND

Thousands of individuals die every year from asphyxiation that results from a blockage of the trachea. The blockage may be due to one of many reasons. For example, the blockage may be a collapse of the trachea due to facial and/or neck trauma or a collection of blood, mucus, bone fragment, teeth, and other substances. The blockage may result from a foreign object such as food or other material.

When a blockage to the trachea occurs, every minute that the individual lacks oxygen is critical. Depriving the brain of oxygen for only a few minutes may result in permanent brain damage or even death. Therefore, treatments such as the Heimlich maneuver and the tracheotomy have been developed.

The Heimlich maneuver requires that a rescuer squeeze the torso of the individual to force out air trapped within the lungs. However, the Heimlich maneuver is generally only successful where the blockage is a foreign object that can be expelled from the trachea by the air being forced from the lungs. Furthermore, the Heimlich maneuver is not always successful even for foreign objects because the object is lodged too tightly and/or because there is an insufficient amount of air trapped within the lungs to be expelled.

The tracheotomy is, heretofore, primarily a surgical procedure that is done by a skilled surgeon within the confines of a hospital or other emergency facility. The conventional tracheotomy requires that an incision be made by a surgeon in the neck of the patient so that an opening to the trachea can be created between the blockage and the lungs to allow the lungs to receive air or other breathable gas. While the conventional tracheotomy is almost always successful at clearing a pathway to the lungs, the delay necessary to transport the individual to an appropriate facility where a conventional tracheotomy may be performed may result in permanent brain damage or death.

SUMMARY

Embodiments of the present invention address these issues and others by providing apparatus and methods that perform a tracheotomy and that do not necessarily require the skill of a surgeon. Thus, the tracheotomy may be provided by a bystander or other individual immediately upon determining that the Heimlich maneuver is unsuccessful or otherwise infeasible. Therefore, it is beneficial to have an embodiment of such a device where blockages are likely to be encountered in the field, such as within restaurants, commercial airplanes, and emergency response vehicles.

One embodiment is an apparatus for performing a tracheotomy. The apparatus includes an applicator base that has an aperture that is located over the trachea upon the applicator base being placed on the neck of a patient. A firing mechanism is fixed relative to the applicator base and has a cutting instrument and grommet such that when the firing mechanism is triggered, the cutting instrument and grommet are propelled through the aperture to puncture the trachea and insert the grommet into the puncture site. An actuator triggers the firing mechanism upon receiving application of manual force by a user.

Another embodiment is an apparatus for performing a tracheotomy. The apparatus includes an applicator base having an aperture and a base assembly fixed relative to the applicator base. The base assembly includes an instrument having a cutting tip on an end closest to the aperture of the applicator base and a grommet having an air passage and being positioned between the cutting tip and the aperture. The air passage is sized such that the cutting tip may pass through the air passage by an amount sufficient to expose at least a portion of the cutting tip beyond the air passage. A biasing element applies force to the cutting instrument and grommet in a direction toward the aperture of the applicator base, and a stop restrains the biasing element from forcing the cutting tip beyond the aperture. An actuator receives manual force from a user and transfers the manual force to the base assembly to release the stop and thereby allow the biasing element to force the cutting tip beyond the aperture and thereby insert the grommet within the trachea.

Another embodiment is a method of performing a tracheotomy utilizing a device that comprises an applicator base having a curvature and an aperture located in the curvature and having a firing mechanism with a cutting instrument and grommet aimed toward the aperture. The method involves tilting the head of the patient back to expose and distend the trachea such that the curvature of the trachea protrudes from the neck of the patient. The method further involves placing the device onto the patient such that the curvature of the applicator base fits to the curvature of the trachea and such that the aperture is located between the larynx and the sternum. The firing mechanism of the device is activated to cause the cutting instrument and grommet to be propelled through the aperture of the applicator base and into the trachea of the patient so as to insert the grommet within the trachea.

DETAILED DESCRIPTION

Embodiments of the present invention provide for a tracheotomy to be performed by utilizing a device that propels a cutting instrument and a grommet into the trachea to thereby insert the grommet in the trachea and provide an unobstructed air passage. Accordingly, because the device itself propels the cutting instrument and grommet, an incision need not be made by a surgeon so that the tracheotomy may be performed without the delay associated with transporting the patient to a surgical facility.

Figure 1:
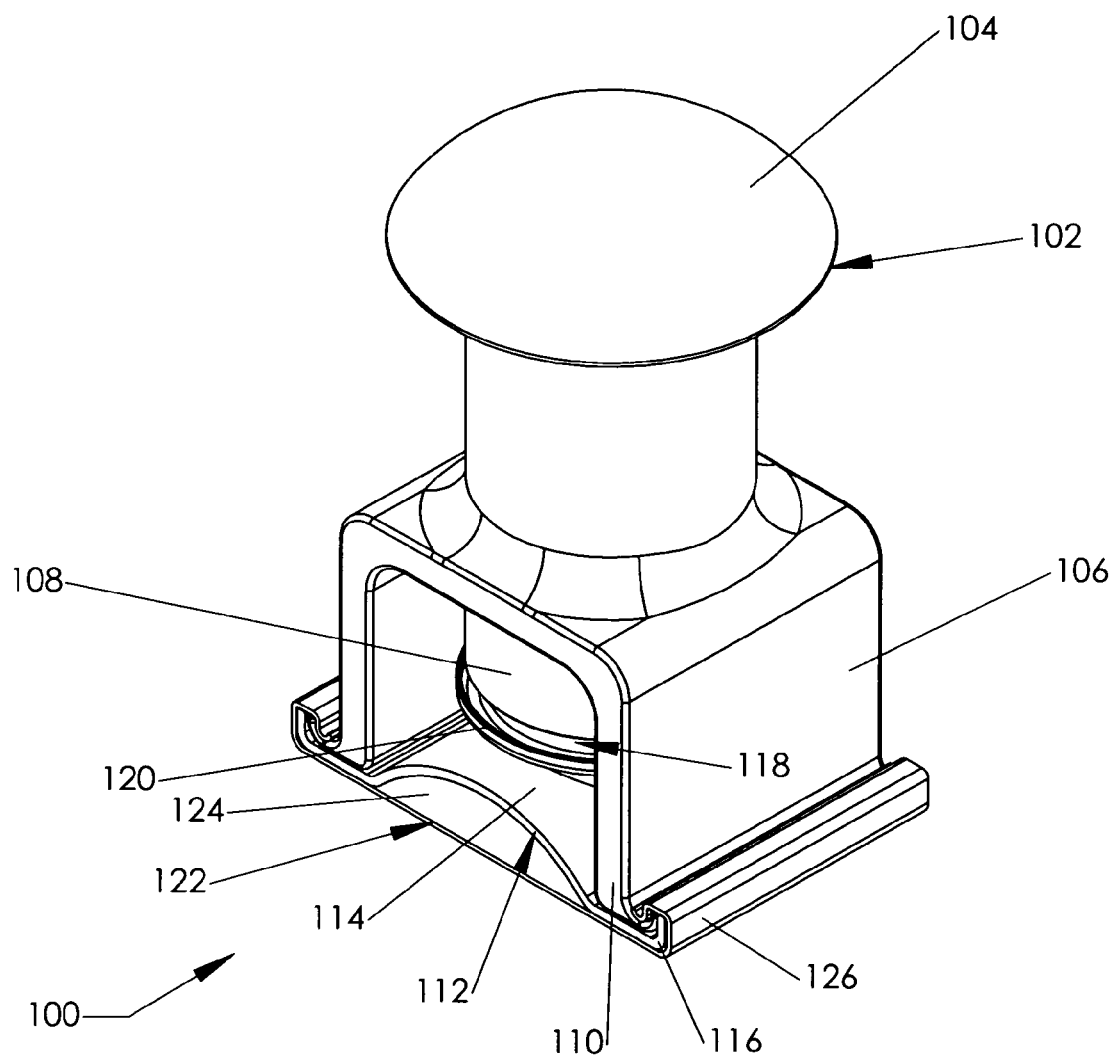
FIG. 1 is a perspective view of one example of an apparatus for performing a tracheotomy.
Figure 2:
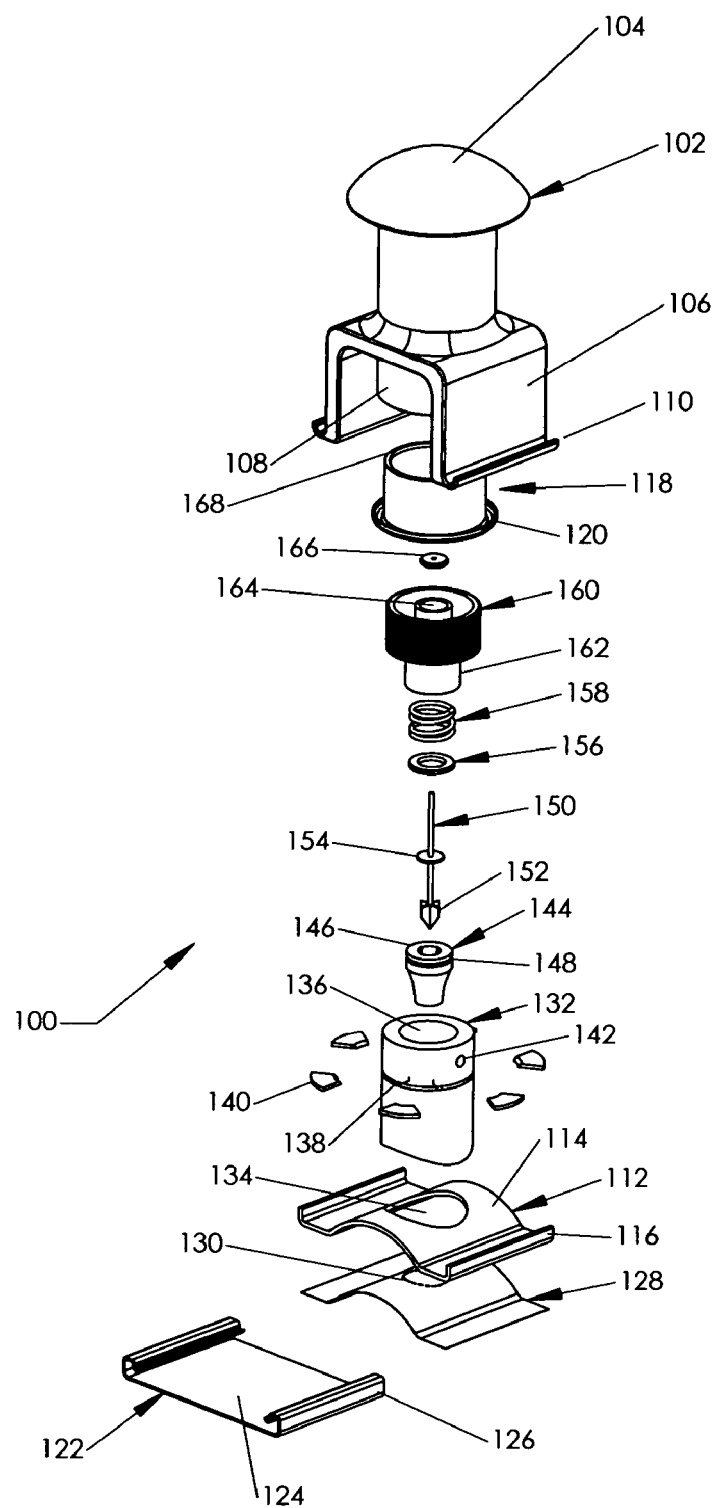
FIG. 2 is an exploded perspective view of the example of the apparatus for performing a tracheotomy.

FIGS. 1 and 2 show one illustrative embodiment of a device for performing a tracheotomy. The device 100 includes an applicator base 112 as a foundation for positioning the device onto the patient. The applicator base 112 of this example includes a portion 114 having curvature and includes an aperture 134 located on the curvature. The portion 114 may be placed over the curvature of the trachea as it protrudes from the neck of the patient. As discussed below, the applicator base 112 of this example bends due to application of force upon an actuator 102 to cause the trachea to be distended and to further expose the curvature. Thus, the curvature of portion 114 and the bending of the applicator base 112 work in conjunction to ensure that the aperture 134 is properly aligned over the trachea of the patient, which thereby eliminates some of the difficulty that might occur in creating an incision at the proper location.

The applicator base 112 of this example also includes flanges 116. The flanges 116 receive flanges 110 of the actuator 102, which is discussed below. The applicator base 112 receives force from the actuator 102 at the flanges 110 which results in the bending of the applicator base 112.

The applicator base 112 may be made of various materials that are relatively rigid. However, for embodiments where it is desired for the applicator base 112 to bend from the force applied to the actuator 102 so as to further distend the trachea, the applicator base 112 should be made of a material having some flexibility. Examples of materials include various types of plastics, woods, metals, and composites.

This example includes an adhesive sheet 128 that is applied to the side of the applicator base 112 that faces the patient. The adhesive sheet 128 is bonded to the applicator base 112 and also includes an adhesive facing away from the applicator base 112 and toward the patient. This adhesive causes the adhesive sheet 128, and hence the applicator base 102, to be adhered to the skin of the patient once the applicator base 112 is positioned onto the neck of the patient. The adhesion serves to hold the applicator base 112 in position relative to the trachea during the tracheotomy process, discussed in more detail below. Further, the applicator base 102 surrounds the incision site as does the adhesive sheet 128 so that the adhesion to the skin prevents leakage of blood resulting from the incision, thereby protecting bystanders from the spatter of blood and other fluids. This adhesion surrounding the incision site also prevents outside contaminants from entering the incision site beneath the applicator base 112. The adhesive sheet 128 may have a protective film adhered to the side facing the patient to prevent contaminants from collecting on the sheet, and the protective film is peeled away immediately prior to attachment to the patient's skin.

The adhesive sheet 128 may have additional substances for aiding in the treatment of the wound created by the tracheotomy process. For example, a triple anti-biotic coating may be located on the adhesive sheet 128 on the side facing the patient in the area adjacent the aperture 134 of the applicator base 112. This coating assists in the prevention of infection at the site of the incision and may also act as a lubricant to assist in making the incision and insertion. As another example, a coagulant gel may be included within a pouch 130 formed within the adhesive sheet and located within the area penetrated during the incision. The coagulant gel is dispersed during the incision and assists in limiting the amount of bleeding that occurs due to the incision.

A mounting base 132 is fixed to the applicator base 112 and provides a support for a firing mechanism that performs the incision. The mounting base 132 of this example is cylindrical with a passage 136. Additionally, the mounting base 132 includes a plurality of slots 138 spaced about the circumference. Each slot 138 receives a retention insert 140 that serves as a stop for the firing mechanism to prevent it from firing until activated by a user, and the use of the retention insert 140 in relation to the firing mechanism is discussed in more detail below. The mounting base 132 may also include a port 142 for receiving an oxygen-rich supply line once the tracheotomy is completed if the patient begins breathing without further assistance. Additionally, internal exhaust ports not visible in FIG. 2 may be included to allow air pressure and fluids to escape upon creating the incision, and these exhaust ports are discussed in more detail below.

The mounting base 132 may also be made of various materials. The mounting base 132 requires no flexure such that a completely rigid structure may be constructed. Examples of materials for the mounting base 132 also include various plastics, woods, metals, and composites.

A grommet 144 is positioned within the passage 136 of the mounting base 132. The grommet 144 is ultimately propelled through the incision and thereby inserted into the trachea. The grommet 144 includes an air passage 146 which provides an unobstructed pathway for a breathing gas once inserted within the trachea. The grommet 144 includes a groove 148 that is engaged by the retention inserts 140 prior to triggering the firing mechanism. The retention inserts 140 hold the grommet in a fixed position.

Figure 9:
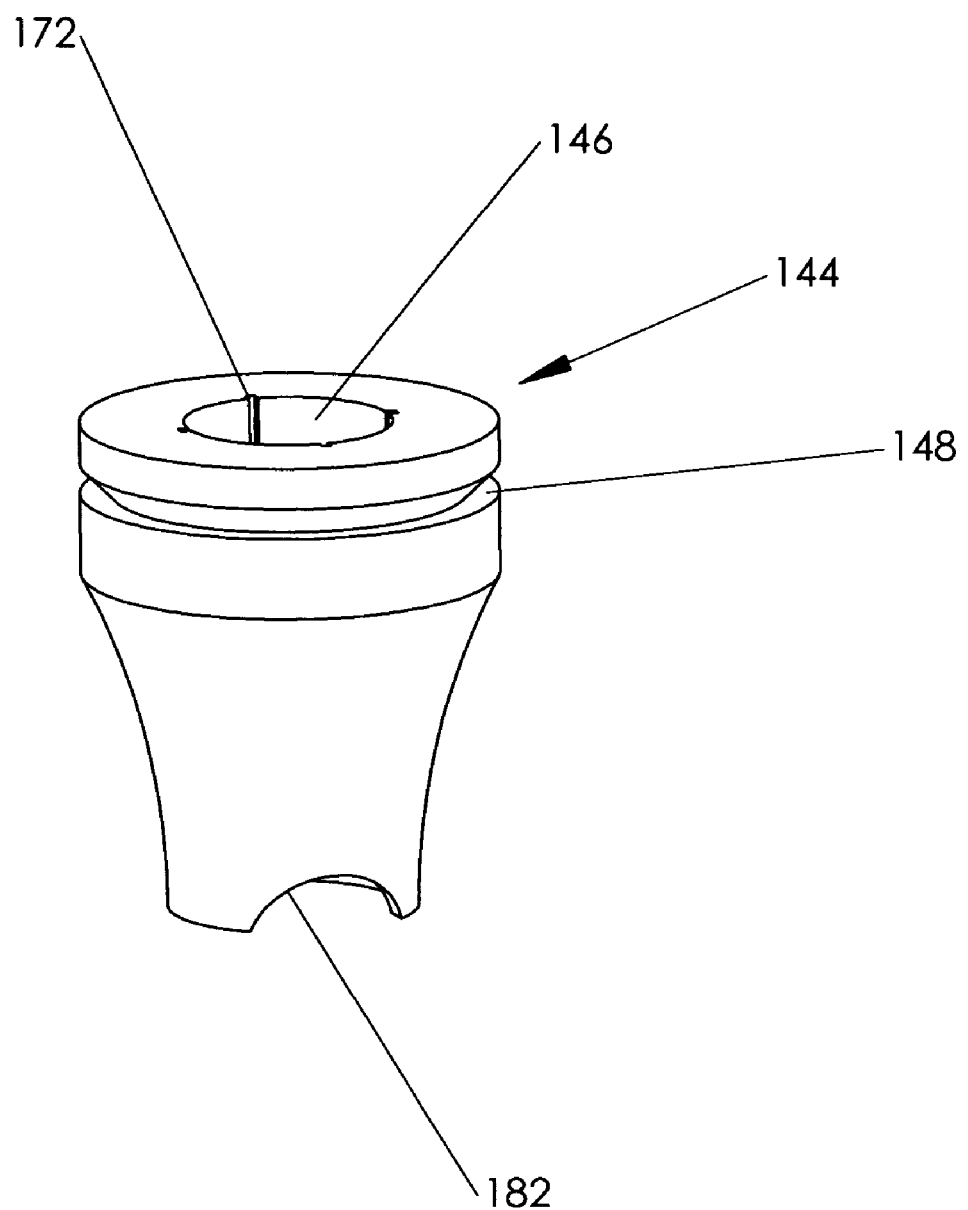
FIG. 9 is a perspective view of an example of a grommet that is inserted into the trachea of a patient by the apparatus.

A more detailed view of the grommet 144 is shown in FIG. 9. In this view, the angular shape of the groove 148 for this example is shown. Grooves 172 within the walls of the passage 146 are also shown. These grooves 172 act as a guide for blades of a broadhead 150 that passes through the grommet 144 during the progression of the firing mechanism.

The grommet 144 may also include a recess 182 that serves to direct airflow. The grommet 144 may be oriented within the device 100 so that the recess 182 faces the direction of the lungs. When inserted into the trachea, recess 182 then directs airflow from passage 146 toward the lungs of the patient to provide more efficient respiration.

The grommet 144 is also a rigid structure, with the groove 148 capable of withstanding the force of the firing mechanism prior to being triggered. Furthermore, the grommet 144 maintains its shape including the air passage while being propelled by the firing mechanism and maintaining the opening within the tissues of the patient. Various materials are also suitable for the grommet 144 but due to direct contact with tissues of the patient, the grommet 144 must be a sterile material such as a plastic or a metal such as stainless steel.

Returning to FIG. 2, a cutting instrument is included in the device to perform the incision of the skin, fascia, and tracheal tissues. The cutting instrument of this example is a broadhead 150 that has a cutting tip 152 with four orthogonal blades. These blades reside within the grooves 172 of the grommet 144. The broadhead 150 includes a drive plate 154 that receives force of the firing mechanism and causes the broadhead 150 to be propelled downward toward and through the aperture 134. Once passing through the aperture, the cutting tip 152 pierces the adhesive sheet 128 and then the skin, fascia, and tracheal tissues to thereby expose the interior of the trachea so that the grommet 144 can then be inserted therein.

Prior to firing, the drive plate 154 of the broadhead 150 is in a joined relationship to a pressure plate 156. The joined relationship of the drive plate 154 to the pressure plate 156 may be accomplished in a variety of ways, such as an adhesive bond, or the two plates may be one integral piece with a weakened area (e.g., perforation) allowing the pressure plate 156 to separate from the drive plate 154 upon application of a particular amount of force to the pressure plate 156 while the drive plate 154 is in a stopped position. However, the joined relationship of the drive plate 154 and the pressure plate 156 must be sufficiently strong to withstand the resistance of the tissues of the patient to piercing by the cutting tip 152.

The broadhead 150 may be made of various materials but has several requirements. The broadhead 150 must be very rigid to avoid flexing during the incision by the cutting tip 152, and the cutting tip 152 must be sufficiently sharp to easily penetrate the skin, fascia, and tracheal tissues. Due to direct contact with tissues of the patient, the cutting tip 152 must also be sterile. Examples of materials include plastics and metals.

The bottom side of the pressure plate 156 abuts the top of the grommet 144 while the top side of the pressure plate 156 is contacted by a biasing element such as a coil spring 158 of this example. The coil spring 158 biases the pressure plate 156 toward the aperture 134, which thereby biases the broadhead 150 and grommet 144 toward the aperture 134 as well. However, the retention inserts 140 hold the grommet 144 in place, which thereby prevents the pressure plate 156 and broadhead 150 from being propelled.

The bias provided by the biasing element, or coil spring 158 of this example, must be sufficient to both propel the cutting tip 152 of the broadhead 150 through the tissues of the patient to reach the interior of the trachea. The bias must also be sufficient to force a substantial portion of the grommet 144 through the incision so that the air passage 146 provides an unobstructed pathway for a breathable gas to reach the interior of the trachea.

The amount of bias may vary depending upon such factors as the size of the cutting tip 152 and grommet 144 and the age of the patient, which are interrelated. The device 100 may be provided in a range of sizes to fit the trachea of the particular patient requiring treatment. For example, the device 100 may be one of three sizes: infant, child, and adult. Each size may have its own size of applicator base 112 and curvature 114 for properly fitting the trachea of the patient, and may also have a particular size of broadhead 150 and grommet 144 and a related spring bias.

A cartridge 160 mounts onto the mounting base 132 by having a smaller diameter portion 162 that fits within the passage 136. The wall of the passage 136 may be threaded and the wall of the portion 162 may also be threaded so that the cartridge 160 screws onto and off of the mounting base 132. The cartridge includes an upper chamber 164 that has a floor, and the coil spring 158 abuts the underside of the floor which provides a stable point from which the spring 158 expands once the firing mechanism is triggered.

Additionally, the upper chamber 164 serves to limit the travel of the broadhead 150. The shaft of the broadhead 150 extends into the chamber 164 and a cap plate 166 is attached to the end of the shaft of the broadhead 150. The floor of the chamber 164 acts as a stop for the cap plate 166 so that once the firing mechanism is triggered and the broadhead 150 is propelled, the cap plate 166 eventually reaches the floor of the chamber 164 and stops the broadhead 150. This stoppage occurs after the broadhead 150 has created the incision. However, at this point, the pressure plate 156 continues to receive force form the spring 158 and breaks free from the drive plate 154 so that the spring 158 continues to propel the grommet 144 into the incision to thereby insert the grommet 144 into the trachea.

The cartridge 160 may also be made of various materials that provide a rigid structure. The cartridge 160 remains fixed to the mounting base 132 while supporting the spring expansion and while also acting as the stop for the broadhead 150. Therefore, the cartridge 160 is constructed of a material that can withstand those forces. Likewise, the connection of the cap plate to the shaft of the broadhead 150 withstands the force required to break the pressure plate 156 free from the drive plate 154. One example of the connection of the cap plate 166 to the broadhead 150 is a threaded engagement.

A retention collar 118 slides over and beyond the cartridge 160 and then over the mounting base 132. The retention collar 118 includes a protrusion 168 on its upper edge that engages the slotted area 138 of the mounting base to hold the retention inserts in place and within the groove 148 of the grommet 148. Therefore, so long as the protrusion 168 is in engagement with the slotted area 138, the firing mechanism is held in an untriggered state with the spring 158 in its compressed state and with the grommet 144 and broadhead 150 suspended above the aperture 134.

The retention collar 118 also includes a flange 120 on its lower edge. The flange 120 is contacted by the actuator 102 after a user has applied manual force to the actuator 102. Once in contact, the manual force applied to the actuator causes the retention collar 118 to begin to slide downward, which removes the protrusion 168 from the slotted area 138. Once this occurs, the force of the spring 158 that is transferred through the pressure plate into the grommet 144 causes the grommet 144 to force the retention inserts 140 outward as the grommet 144 begins to move downward. The grommet 144 and broadhead are propelled downward through the aperture 134 by the spring force.

The retention collar 118 may be made of various materials, but is sized so as to slide over the cartridge 160 and onto the mounting base 132. Furthermore, the retention collar 118 and protrusion 168 are sized so that the protrusion seats firmly within the slotted area 138. The retention collar 118 is constructed of a material that is relatively rigid, to avoid flexure that would otherwise allow for the release of the retention inserts 140. However, the retention collar 118 does flex enough to allow the protrusion to become unseated form the slotted area 138 upon application of sufficient force from the actuator 102. Examples of materials for the retention collar 118 include various plastics.

The actuator 102 receives the direct application of force by the user that causes the firing mechanism to trigger. However, the force provided by the user is isolated from the force applied to the grommet 144 and broadhead 150. Therefore, no skill is necessary in determining how to create the incision and insert the grommet 144. Instead, the user need only be concerned with aligning the applicator base 112 with the trachea and then applying enough force to trigger the firing mechanism.

The actuator 102 of this example has a mushroom-shaped portion 104 suitable for a user to apply a downward force by hand. While shown as a mushroom-shaped handle 104, it will be appreciated that various other shapes and styles of handles allowing a user to apply manual downward force are also applicable. In addition to the portion 104, the actuator 102 includes legs 106 that include flanges 110 formed at the bottoms. An inner hollow cylinder 108 extends downward between the legs 106 but does not extend the full length of the legs 106.

The actuator 102 is a rigid structure that receives the manual force form the user and transfers the force to the flange 120 of the retention collar 118 and to the flange 116 of the applicator base 112. The actuator 102 may be constructed of various materials and examples include plastics, wood, metal, or composites.

In operation, once the user begins applying manual force to the handle 104 of the actuator 102, the flange 110 of legs 106 engage the flange 116 of the applicator base 112 to force it to bend and thereby further distend the trachea to prepare it for receiving the broadhead 150 and grommet 144. The cylinder 108 then engages the flange 120 of the retention collar 118 to force it downward and thereby trigger the firing mechanism by releasing the retention inserts 140 previously acting as a stop against the groove 148 of the grommet 144. The operation of the device 100 is discussed in greater detail below with reference to the cross-sectional views of FIGS. 3–7.

In FIG. 1, the device 100 is shown in a fully assembled state ready for use. However, it may be desirable to store the device in a partially disassembled state and within sterile packaging prior to use. For example, the actuator 102 may be stored independently of the remainder of the device 100 to prevent inadvertent triggering of the firing mechanism.

When the device 100 is being stored in an assembled state as in FIG. 1, it may be desirable to utilize a safety clip 122 to prevent the actuator 102 from moving in relation to the remainder of the device to prevent inadvertent triggering and to prevent inadvertent contact with the cutting instrument. The safety clip 122 of this example attaches by sliding over the flanges 110 of the actuator 102 that are abutting the flanges 116 of the applicator base 112. When it is time to use the device 100, the safety clip 122 is removed from the device 100 simply by sliding the safety clip 122 off of the flanges 110 and 116.

FIGS. 3–7 are cross-sectional views of the device 100 installed on the neck 200 of a patient requiring a tracheotomy. These cross-sectional views illustrate the assembled relationships of the components illustrated in FIG. 2 and also illustrate the sequence of events that occur within the device 100 to provide for the incision and subsequent insertion of the grommet 144.

In one illustrative example of a tracheotomy process utilizing the device 100, a user, preferably wearing protective gloves, places the patient on his or her back. The user locates the general area of penetration above the sternum bone and below the larynx and sterilizes the area using an alcohol swab. The appropriately sized device 100 is removed from its sterile packaging and the safety clip 122 is removed from the device 100. The actuator cup 102 is placed to the side separately from the remainder of the device 100, and the protective film is removed from the applicator base adhesive 128.

The user then finds the proper area for the incision by finding the midline of the trachea that is approximately one-half inch above the sternum bone. An object such as a pillow, if available, may be placed under the back of the patient's neck to assist in lifting the neck to cause the curvature of the trachea to protrude. The unit is then placed firmly upon the midline of the trachea with the curvature 114 of the applicator base 112 aligning with the curvature of the protruding trachea.

Once the applicator base 112 and related assembly has been installed, the user grasps the handle 104 with his or her dominant hand and then grasps the back of the neck of the patient with the other hand. The user lifts up on the back of the neck of the patient to thereby tilt back the head and further distend the trachea 206. The user then slowly slides the actuator 102 back onto the assembly, exercising care to ensure that the flanges 110 of the actuator are in proper alignment with the flanges 116 of the applicator base 112.

Figure 3:
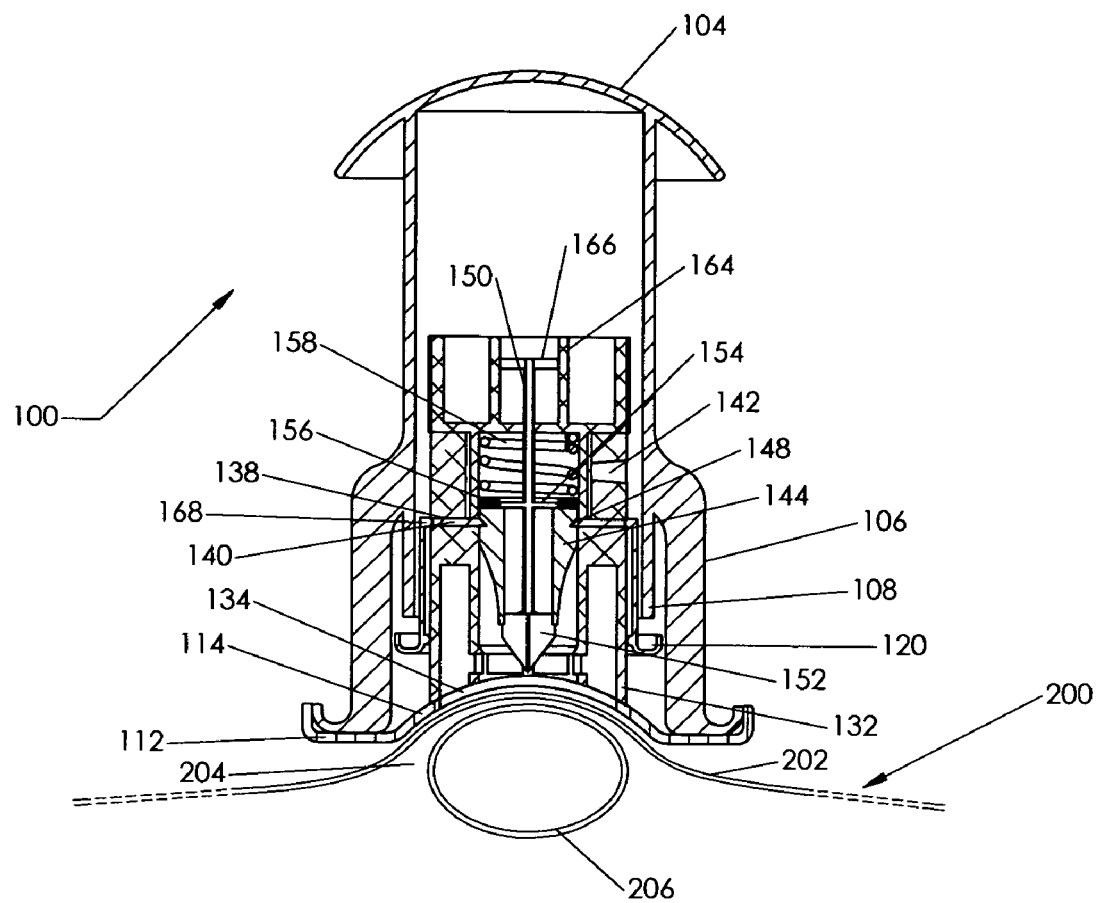
FIG. 3 is a cross-sectional view of the example of the apparatus in a resting state when initially placed onto the neck of the patient.

FIG. 3 is a cross-sectional view of the device 100 once it has been installed as previously discussed and is ready to begin receiving manual force upon the handle 104 from the user. The frontal region of the neck 200 of the patient including the skin 202, fascia 204, and trachea 206 is also shown in cross-section in FIGS. 3–7 to illustrate the incision into the interior of the trachea 206 and to further illustrate the insertion of the grommet 144 into the interior of the trachea 206.

In FIG. 3, the device 100 is in a resting state, with no manual force being applied to handle 104 of the actuator 102. In this resting state, the aperture 134 of the applicator base 112 is positioned directly over the trachea, with the portion 114 having its curvature in a concentric relationship to the curvature of the trachea 206. However, because no manual force has yet been applied to the actuator 102, the applicator base 112 is not yet bent to further distend the trachea 206.

Further, the firing mechanism is in an untriggered resting state, with the protrusion 168 of the retention collar 118 being firmly seated against slotted area 138 to thereby hold the retention inserts 140 firmly against the groove 148 of the grommet 144. The retained grommet 144 maintains the pressure plate 156 and joined driving plate 154 in the suspended position, with the coil spring remaining compressed against the underside of the cartridge 160. The cap plate 166 is suspended above the floor of the upper chamber 164.

Once the user is ready to trigger the device to perform the incision and insertion of the grommet 144 into the trachea 206, the user begins to squeeze slowly but firmly between both hands, one on the handle 104 and one on the backside of the patient's neck. The user attempts to minimize any lateral movements to maintain the alignment of the aperture 134 over the trachea 206. This squeezing action sets several events into motion.

Figure 4:
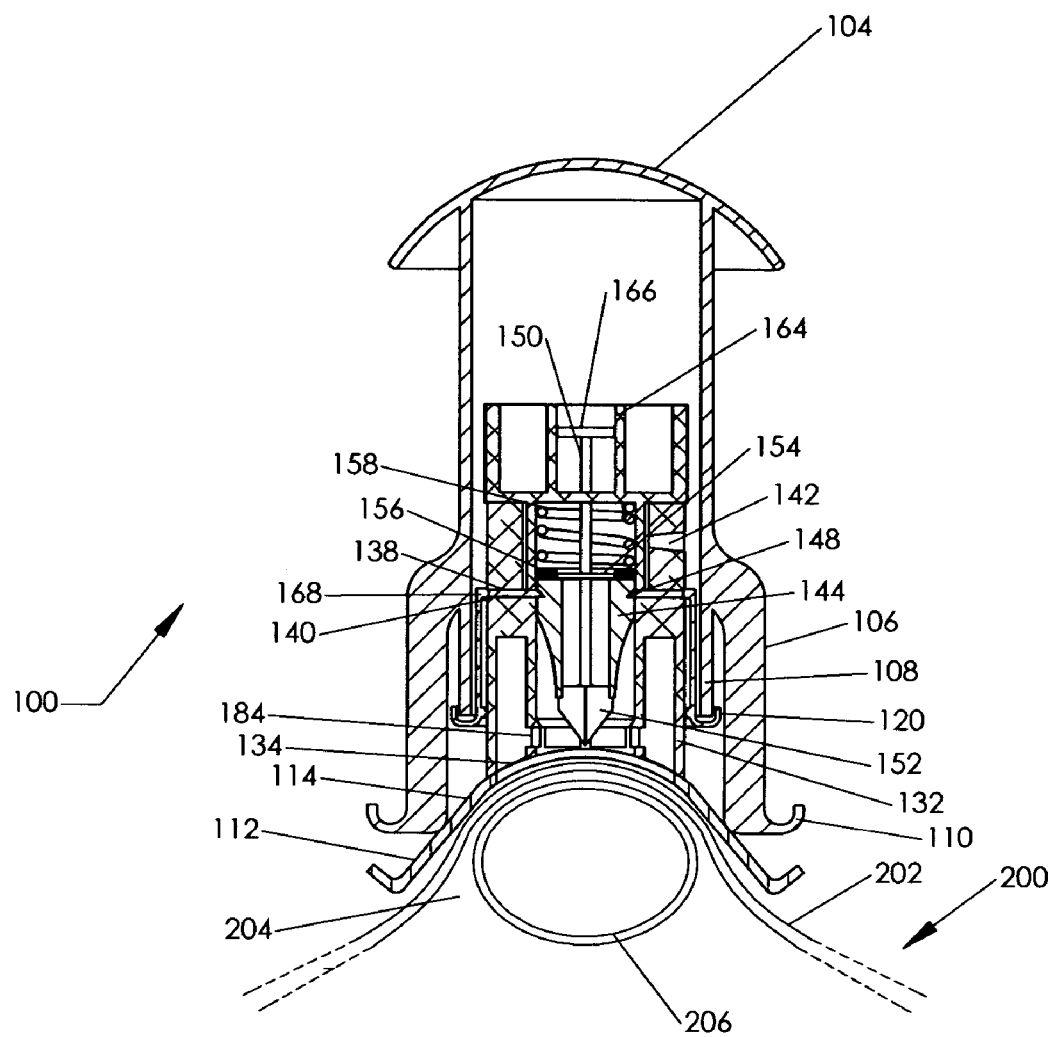
FIG. 4 is a cross-sectional view of the example of the apparatus in a pre-fire state as the user has begun to apply manual force but a firing mechanism has not yet been triggered.

In FIG. 4, the device 100 is an unfired state but with manual force being initially applied to handle 104 of the actuator 102. The actuator 102 has moved downward so that flange 110 has contacted the applicator base 112 and caused it to bend inward. The inward bend of the applicator base 112 has pressed inward on the tissue surrounding the trachea 206 so as to distend the trachea 206. The distended trachea 206 is snugly positioned within the confines of the bent applicator base 112, which ensures alignment of the cutting instrument 150 and grommet 144 and also resists lateral movement of the device 100 relative to the trachea 206.

The firing mechanism remains in an untriggered resting state, as the inner cylinder 108 of the actuator 102 has just reached the flange 120 of the retention collar 118 but has not yet forced the retention collar 118 to slide downward so that the protrusion remains firmly seated in the slotted area 138 against the retention inserts 140. In this untriggered state, exhaust ports 184 of an inner cylinder of the mounting base 132 are open in preparation for exhausting any air pressure or bodily fluids resulting from the downward movement of the broadhead 150 and grommet 144 once they are fired.

Figure 5:
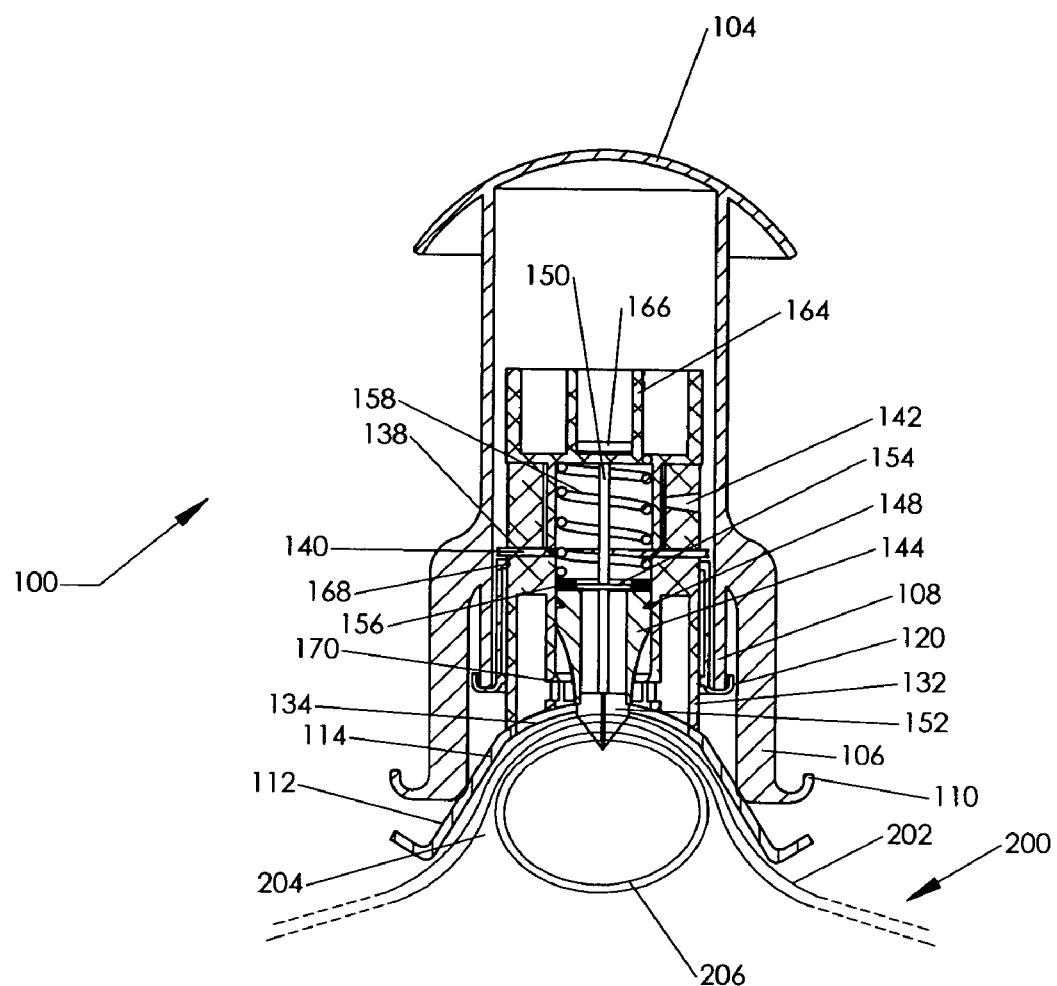
FIG. 5 is a cross-sectional view of the example of the apparatus in a mid-stroke state after the user has applied enough manual force to trigger a firing mechanism.

In FIG. 5, the manual force being applied to the handle 104 of the actuator 102 has caused the inner cylinder 108 of the actuator 102 to press against the flange 120 of the retention collar and slide it downward, thereby no longer maintaining the protrusion 160 in the slotted area 138. The retention inserts 140 have backed out of the slots and have separated from the groove 148 of the grommet 144 in response to the pressure being applied by the spring 158 onto the grommet 144.

As shown in FIG. 5, the firing mechanism has been triggered by the release of the retention inserts 140 allowing the spring 158 to expand, thereby propelling the broadhead 150 and the grommet 148 downward under the force being exerted by the spring 158 as opposed to force from the user. At this point, the firing mechanism is in mid-stroke, as the broadhead tip 152 has penetrated the tissues of the patient and has reached the interior of the trachea 206. In embodiments where the cutting tip 152 is a set of orthogonal blades as shown, the incision is a cross-pattern that facilitates the insertion of the grommet 144. However, at this mid-stroke point, the grommet 144 has not yet reached the incision site.

To prevent the cutting tip 152 from penetrating too deeply and potentially puncturing the trachea on the back side, the cap plate 166 reaches the bottom of the upper chamber 164 and thereby stops further downward movement by the broadhead 150. However, the spring 158 continues to apply force to the pressure plate 156 so that once the cap plate 166 bottoms and the broadhead 150 stops, the pressure plate 156 continues to move by breaking free from the drive plate 154. This is shown in FIG. 6.

Figure 6:
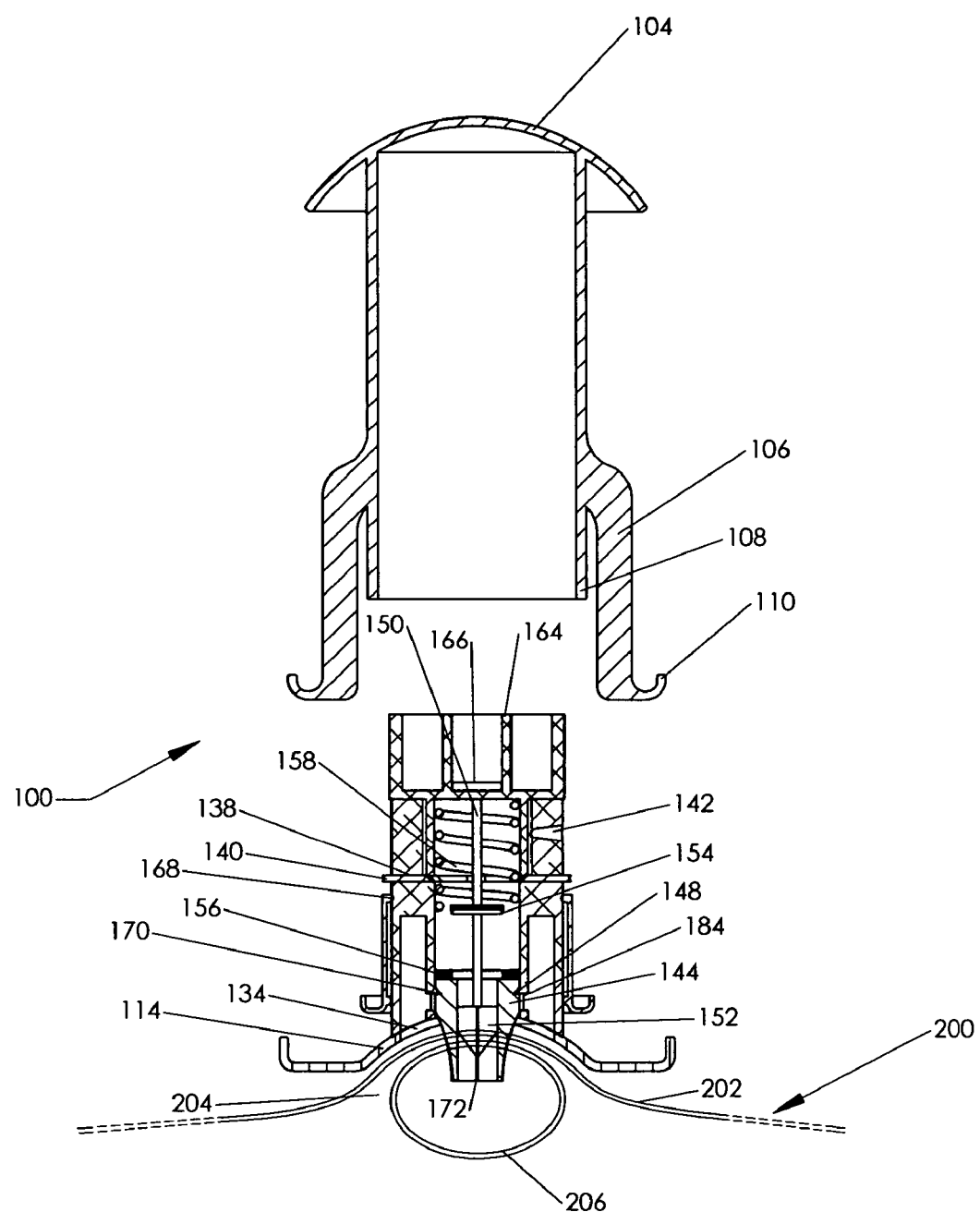
FIG. 6 is a cross-sectional view of the example of the apparatus in a fully extended and locked state with the actuator being removed.

In FIG. 6, the firing mechanism has completed a full stroke by the pressure plate 156 breaking free and continuing to be propelled, along with the grommet 144, toward and through the aperture 134. The spring 158 continues to force the grommet 144 downward and forces the grommet 144 into the incision. The grommet 144 reaches a locked position upon the groove 148 of the grommet 144 engaging a protrusion 170 of the inner cylinder of the mounting base 132. Once the grommet 144 reaches the locked position by the engagement of the protrusion 170 with the groove 148, it is held in place within the trachea 206 regardless of whether force from the spring 158 is continuing to be applied.

Figure 7:
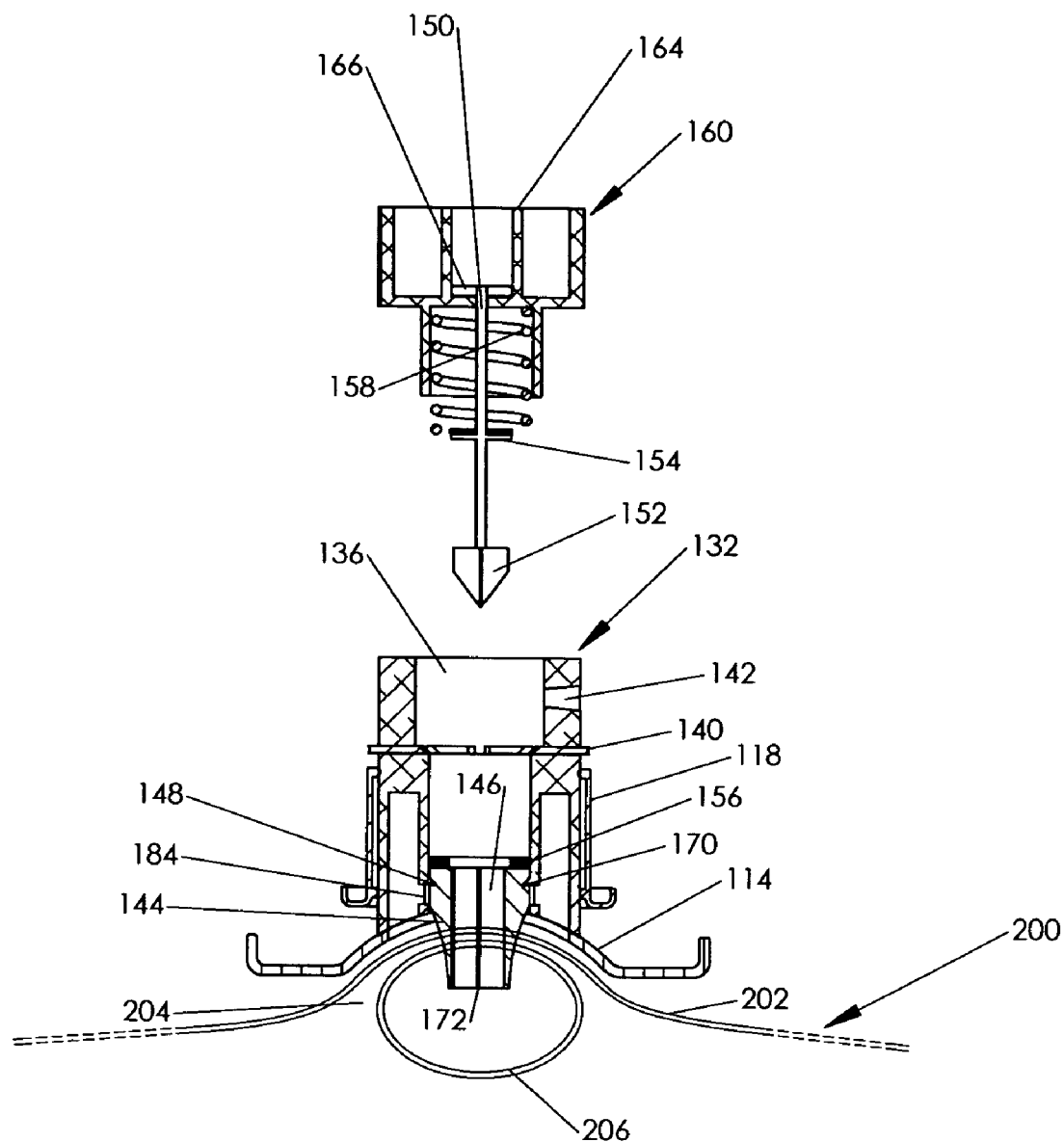
FIG. 7 is a cross-sectional view of the example of the apparatus in a final state whereby a cartridge containing the firing mechanism has been removed.

Furthermore, as the grommet 144 is approaching the locked position, the exhaust ports 170 become blocked to thereby lock in any fluids or other substances that have been exhausted through the ports 170 during the incision process. As shown in FIG. 7, once the grommet 144 reaches the locked position, the exhaust ports 170 are completely blocked by the grommet 144.

Once the grommet 144 has been inserted into the trachea 206, the device 100 may be partially disassembled to provide access to the air passage 146 leading to the interior of the trachea 206. The first disassembly step involves sliding the actuator 102 from the mounting base by pulling upward on the handle 104. The remainder of the disassembly is shown in FIG. 7. Prior to further disassembly, it may be desirable to tape down the applicator base 112 onto the neck 200 of the patient to provide further stability for the assembly so that the assembly does not move due to subsequent actions including further disassembly, suctioning, connection of breathing assistance equipment, and transportation of the patient.

In FIG. 7, the cartridge 160 including the spring 158 and broadhead 150 are removed by detaching the cartridge 160 from the mounting base 132. As discussed above, the cartridge 160 may be attached to the mounting base by a threaded engagement so that the cartridge 160 is removed by unscrewing the cartridge 160 from the mounting base 132. The cartridge 160 maybe unscrewed by placing an index finger and thumb on each side of the applicator base 112 to further stabilize it while the other hand unscrews the cartridge 160. The cartridge 160 including the attached broadhead 150 and spring 158 may then be placed into a container for sharp objects.

Once the cartridge 160 has been removed, the passage 136 through the mounting base 132 provides access to the grommet 144. At this time, the patient can be treated for excessive bleeding such as by using a French catheter to suction the airway 146 of the grommet 144. Breathing assistance and medication may also be provided via the airway 146. If the patient is beginning to breathe, an oxygen supply tube may be inserted into the oxygen port 142 to provide oxygen saturation while the patient breathes the ambient air. If the patient is not beginning to breathe, then a bag valve mask adapter 174 shown in FIG. 8 may then be installed within the passage 136 of the mounting base 132.

Figure 8:
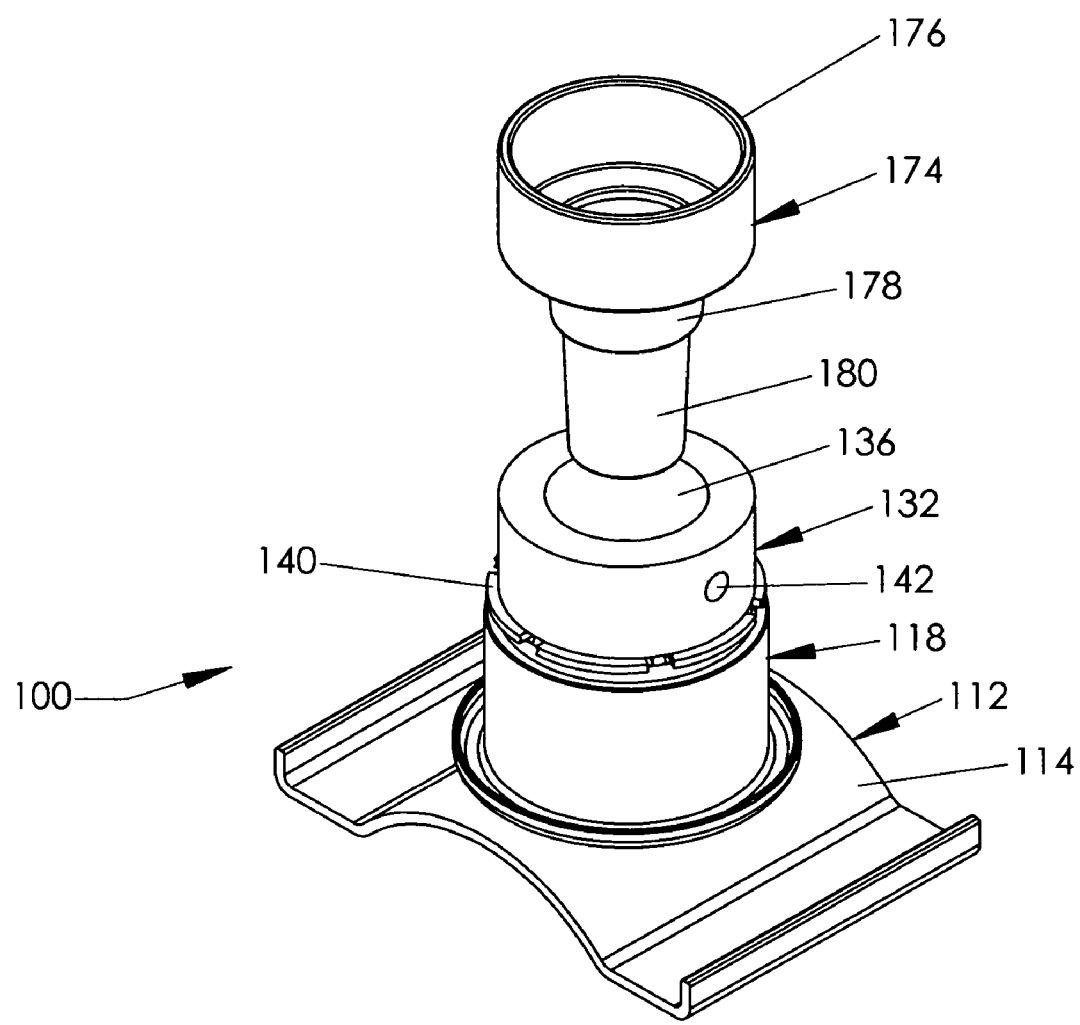
FIG. 8 is a perspective view of the example of the apparatus showing the installation of a bag valve mask assembly.

The bag valve mask adapter 174 of FIG. 8 is installed in the same way and in place of the cartridge 160. The lower portion 180 extends into the bottom of the passage 136 of the mounting base 132 so as to channel airflow directly into the passage 146 of the grommet 144. The middle portion 178 may include threads so that the adapter 174 can be screwed into the passage 136 while the free hand provides further stability to the applicator base 112, and once installed the middle portion 178 seals off the oxygen port 142. The upper portion 176 is sized to engage a bag valve mask so that positive pressure ventilation of air can be provided to the patient.

The patient may then be transported to the emergency facility immediately while the assembly remains attached and the air passage 146 of the grommet 144 continues to channel air into the trachea 206 and lungs of the patient. Accordingly, the patient may be saved by having airflow supplied through the air passage 146 much sooner than if the tracheotomy was performed only after the patient had been transported to a surgical facility.

While the invention has been particularly shown and described with reference to various embodiments thereof, it will be understood by those skilled in the art that various other changes in the form and details may be made therein without departing from the spirit and scope of the invention.

What is claimed is:

1. An apparatus for performing a tracheotomy, comprising:
   an applicator base that has an aperture that is located over the trachea upon the applicator base being placed on the neck of a patient;
   a firing mechanism fixed relative to the applicator base and having a cutting instrument and grommet such that when the firing mechanism is triggered, the cutting instrument and grommet are propelled through the aperture to puncture the trachea and insert the grommet into the puncture site; and
   an actuator that triggers the firing mechanism upon receiving application of manual force by a user;
   wherein the applicator base comprises means for aligning the applicator base and the aperture to the trachea and means for distributing manual force applied to the actuator to the neck of the patient on each side of the trachea to resist lateral movement of the applicator base relative to the trachea during the triggering of the firing mechanism.

2. The apparatus of claim 1, further comprising:
a cylindrical mounting base extending from the applicator base and having a passage in alignment with the aperture, the mounting base having a plurality of slots around the periphery;
wherein the firing mechanism comprises:
a plurality of retention inserts disposed within the slots of the mounting base, the retention inserts contacting the grommet to hold the grommet and cutting instrument in a fixed position,
a cylindrical retention collar concentrically disposed about the cylindrical mounting base, the cylindrical retention collar having a protrusion that is seated within the slots of the mounting base to hold the retention inserts against the grommet, and
wherein manual force to the actuator triggers the firing mechanism by moving the cylindrical retention collar so that the protrusion releases from the slot, allowing the retention inserts to move away from the grommet as the grommet and cutting instrument are propelled through the aperture.

3. The apparatus of claim 2, wherein the cutting instrument is a broadhead having a shaft with a drive plate, wherein the biasing element is a coil spring applying force to a pressure plate in contact with the grommet and attached to the drive plate.

4. The apparatus of claim 3, further comprising a cylindrical cartridge that includes one passage having a floor with an aperture, wherein the shaft of the broadhead passes through the aperture of the floor, wherein the shaft of the broadhead includes a cap plate, wherein the cap plate is larger than the aperture of the floor such that the floor of the cartridge stops movement of the broadhead upon the cap plate contacting the floor, and wherein the pressure plate breaks free from the drive plate upon the cartridge stopping movement of the broadhead such that the coil spring and pressure plate continue to move the grommet through the aperture.

5. The apparatus of claim 4, wherein the grommet contacts a catch at the mounting base to lock the grommet in position relative to the mounting base after being propelled through the aperture by the biasing element.

6. The apparatus of claim 5, wherein the actuator is removable from the retention collar, and wherein the cartridge is removable from the mounting base.

7. The apparatus of claim 6, further comprising a bag valve mask adapter that is attachable to the mounting base upon removal of the cartridge.

8. The apparatus of claim 1, wherein application of manual force to the actuator causes a portion of the actuator to contact the applicator base prior to triggering the firing mechanism so as to bend the applicator base and thereby distend the trachea.

9. The apparatus of claim 1, further comprising a safety clip that is slidably removable from the applicator base and that covers the area of the applicator base where the aperture is located.

10. An apparatus for performing a tracheotomy, comprising:
an applicator base having an aperture and having a curvature where the aperture is located within the curvature and wherein the curvature is surrounded by two planar regions that are flexible relative to the curvature;
a base assembly fixed relative to the applicator base, the base assembly comprising:
an instrument having a cutting tip on an end closest to the aperture of the applicator base;
a grommet having an air passage and being positioned between the cutting tip and the aperture, the air passage being sized such that the cutting tip may pass through the air passage by an amount sufficient to expose at least a portion of the cutting tip beyond the air passage;
a biasing element applying force to the cutting instrument and grommet in a direction toward the aperture of the applicator base;
a stop restraining the biasing element from forcing the cutting tip beyond the aperture; and
an actuator that receives manual force from a user and transfers the manual force first to the planar regions to cause bending of the planar regions relative to the curvature and next to the base assembly to release the stop and thereby allow the biasing member to force the cutting tip beyond the aperture and to thereby insert the grommet within the trachea.

11. The apparatus of claim 10, wherein the biasing member comprises a coil spring.

12. The apparatus of claim 10, further comprising a base adhesive sheet disposed on a side of the applicator base opposite the base assembly, the applicator base and adhesive sheet providing isolation at the incision site to thereby prevent blood splatter from escaping.

13. The apparatus of claim 12, wherein the base adhesive sheet comprises an antibiotic coating.

14. The apparatus of claim 12, wherein the base adhesive sheet comprises a coagulant pouch in alignment with the aperture and tip of the cutting instrument.

15. The apparatus of claim 10, wherein the base assembly further comprises:
a mounting base fixed relative to the applicator base and having slots;
a retention collar disposed about the mounting base, the retention collar having a lip; and
wherein the stop comprises retention inserts disposed within the slots of the mounting base, wherein the retention inserts are held in place by the lip of the retention collar, and wherein the stop is released by the manual force applied to the actuator causing the actuator to contact and move the retention collar to allow the retention inserts to be displaced.

16. The apparatus of claim 10, wherein the curvature fits to a curvature of a trachea when protruding from the neck of a patient.

17. The apparatus of claim 10, wherein bending of the planar regions of the applicator base distends the trachea.

18. A method of performing a tracheotomy utilizing a device that comprises an applicator base having a curvature, planar regions on each side of the curvature, and an aperture located in the curvature and having a firing mechanism with an actuator and with a cutting instrument and grommet aimed toward the aperture, comprising:
tilting the head of the patient back to expose and distend the trachea such that the curvature of the trachea protrudes from the neck of the patient;
placing the device onto the patient such that the curvature of the applicator base fits to the curvature of the trachea and such that the aperture is located between the larynx and the sternum; and
applying manual force to the actuator to first bend the planar regions inward to apply force to the neck of the patient on each side of the trachea to thereby distend the trachea while resisting lateral movement of the device relative to the trachea and to next activate the firing mechanism of the device to cause the cutting instrument and grommet to be propelled through the aperture of the applicator base and into the trachea of the patient so as to insert the grommet within the trachea.

19. The method of claim 18, further comprising applying manual pressure to the back of the neck of the patient and wherein activating the firing mechanism comprises applying manual pressure to an actuator of the device in the direction toward the neck of the patient.

20. The method of claim 18, wherein the device further comprises a cartridge containing the firing mechanism, the method further comprising removing the cartridge and introducing a supply of breathable gas to an air passage of the grommet.

* * * * *